(12) United States Patent
Christensen

(10) Patent No.: US 6,978,188 B1
(45) Date of Patent: Dec. 20, 2005

(54) METHOD FOR CONTOURING BONE RECONSTRUCTION PLATES

(75) Inventor: Andrew M. Christensen, Littleton, CO (US)

(73) Assignee: Medical Modeling, LLC, Golden, CO (US)

(*) Notice: Subject to any disclaimer, the term of this patent is extended or adjusted under 35 U.S.C. 154(b) by 83 days.

(21) Appl. No.: 10/676,594

(22) Filed: Sep. 30, 2003

Related U.S. Application Data

(60) Provisional application No. 60/414,583, filed on Sep. 30, 2002.

(51) Int. Cl.[7] ............ A61F 17/56; G06F 19/00
(52) U.S. Cl. ............ 700/118; 700/163; 606/53; 606/69; 128/898; 433/213; 264/16
(58) Field of Search ............ 700/38, 118, 163; 606/53, 60, 69, 88; 128/898; 433/213; 264/16

(56) References Cited

U.S. PATENT DOCUMENTS 5,370,692 A * 12/1994 Fink et al. .................. 128/898
5,372,598 A * 12/1994 Luhr et al. .................. 606/69
5,413,577 A * 5/1995 Pollock ....................... 606/69
5,779,833 A * 7/1998 Cawley et al. ............ 156/89.11
6,325,803 B1 * 12/2001 Schumacher et al. ......... 606/71

\* cited by examiner

Primary Examiner—Jayprakash N. Gandhi
(74) Attorney, Agent, or Firm—Faegre & Benson, LLP

(57) ABSTRACT

Systems and methods are provided for designing and producing custom-made templates for implantation or for pre-contouring metallic or polymer implantable plates prior to surgery. According to one embodiment, medical image data representing surrounding portions of a patient's anatomy to be repaired by surgical implantation of a bone reconstruction plate is received. Next, three-dimensional surface reconstruction is preformed based on the medical image data. Virtual removal of a bone or portion thereof to be reconstructed is performed with reference to the medical image data by simulating the contemplated surgical implantation procedure. Then, a representation of a template is created that is countered to fit the patient's anatomy to be repaired. Finally, a replica of the template is produced by using Solid Freeform Fabrication manufacturing techniques.

1 Claim, 2 Drawing Sheets

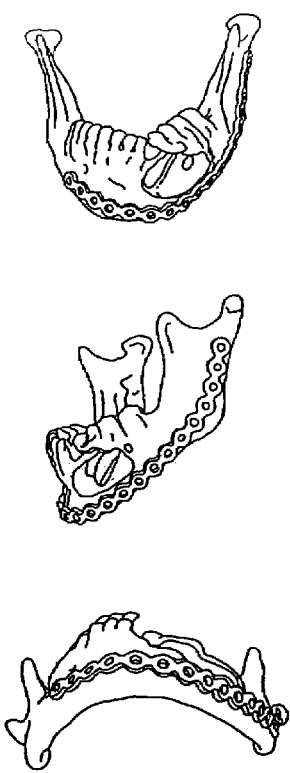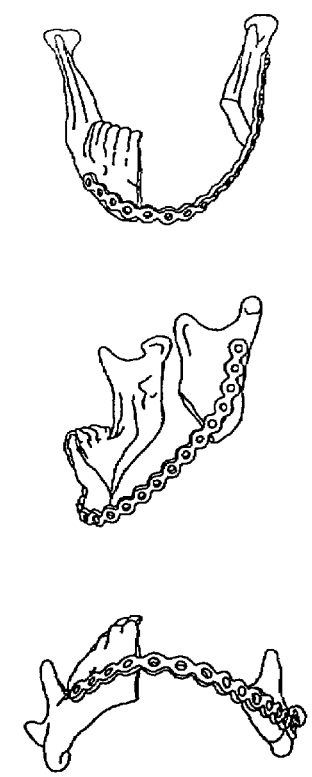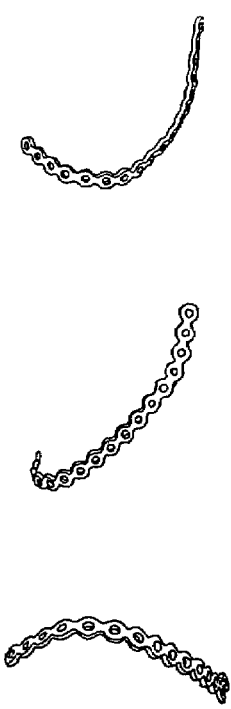

METHOD FOR CONTOURING BONE RECONSTRUCTION PLATES

This application claims the benefit of U.S. Provisional Application No. 60/414,583, filed Sep. 30, 2002, entitled "Method for Contouring Bone Reconstruction Plates" which is hereby incorporated by reference in its entirety.

COPYRIGHT NOTICE

Contained herein is material that is subject to copyright protection. The copyright owner has no objection to the facsimile reproduction of the patent disclosure by any person as it appears in the Patent and Trademark Office patent files or records, but otherwise reserves all rights to the copyright whatsoever.

BACKGROUND

Field

Embodiments of the present invention relate generally to rigid fixation. More particularly, embodiments of the present invention relate to bone reconstruction plates and techniques for producing computer-designed, custom-made templates for implantation or for pre-contouring metallic or polymer implantable plates prior to surgery.

DESCRIPTION OF THE RELATED ART

Surgical procedures are performed routinely in the US for reconstruction of a patient's anatomy after a traumatic injury, congenital disease or other pathology. Many procedures rely on the surgeon's use of metallic (e.g., titanium, titanium alloy, stainless steel and cobalt-chrome) or polymer (e.g., PLA and PLGA) plates and screws (referred to as rigid fixation) to reset bone segments after surgery. These plates function to take the load of the bone segment that is no longer there. The rigidity allows for the patient to heal in the proper position and minimizes motion, thus promoting quick healing and pain reduction after surgery.

These plates are very strong and require bending at the time of surgery with the patient's anatomy as a reference. Many times an aluminum or tin "template" is conformed to the patient's anatomy and then used as a pseudo-template for contouring the plate. For a typical surgeon this process of bending the plate can take 30 to 60 minutes of operating room time, which is very costly. The bending of the plate at the time of surgery also does not allow for contouring to match the patient's other side and can leave a less than desirable final result. The strongest plates, and thus the hardest to bend, are for reconstruction of defects in the spine, pelvis and mandible.

BRIEF DESCRIPTION OF THE SEVERAL VIEWS OF THE DRAWINGS

Embodiments of the present invention are illustrated by way of example, and not by way of limitation, in the figures of the accompanying drawings and in which like reference numerals refer to similar elements and in which:

FIG. 5 illustrates a computer model of the plate bent to the contour of the mandible over the defect according to one embodiment of the present invention.

FIG. 6 illustrates a computer model of the plate bent to the mandible without the pathologic bone in place according to one embodiment of the present invention.

FIG. 7 illustrates a computer representation of the "bent" plate according to one embodiment of the present invention.

SUMMARY

Figure 1:
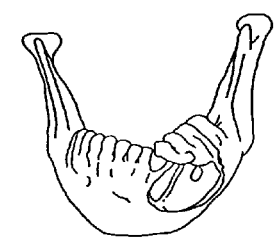
FIG. 1 illustrates a computer model of the bone structure of a patient with a tumor in the left side of the mandible.
Figure 1:
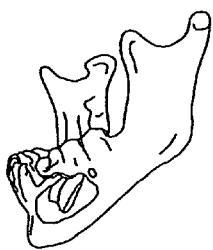
Figure 1:
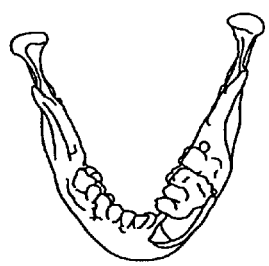
Figure 2:
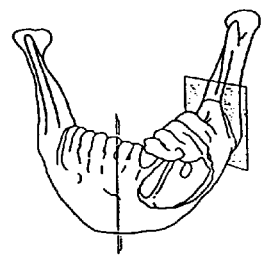
FIG. 2 illustrates a computer model of the resection planes around the tumor in the mandible showing what bone will be removed in surgery.
Figure 2:
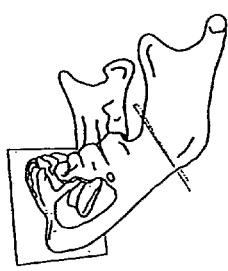
Figure 2:
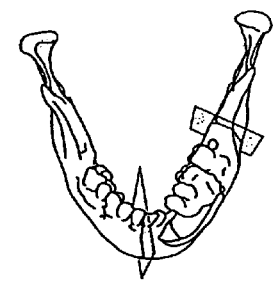
Figure 3:
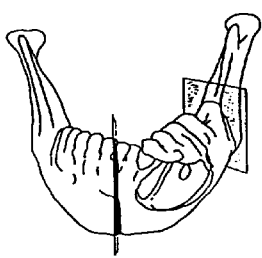
FIG. 3 illustrates a surgical computer simulation, removal of the bone segment and remaining two bone segments according to one embodiment of the present invention.
Figure 3:
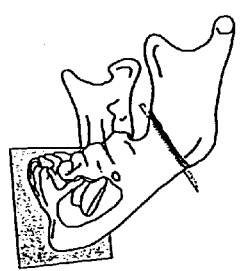
Figure 3:
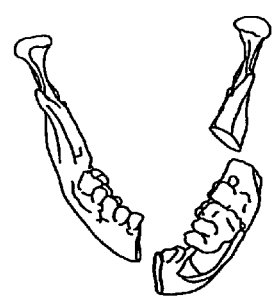
Figure 4:
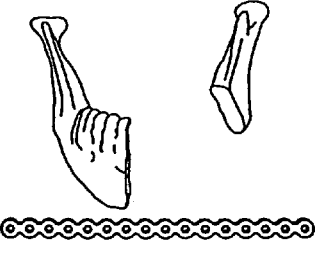
FIG. 4 illustrates a computer representation of the plate next to the mandible that will be reconstructed.

Systems and methods for designing and producing custom-made templates for implantation or for pre-contouring metallic or polymer implantable plates prior to surgery are described. According to one embodiment, medical image data representing surrounding portions of a patient's anatomy to be repaired by surgical implantation of a bone reconstruction plate is received. Next, three-dimensional surface reconstruction is preformed based on the medical image data. Virtual removal of a bone or portion thereof to be reconstructed is performed with reference to the medical image data by simulating the contemplated surgical implantation procedure. Then, a representation of a template is created that is contoured to fit the patient's anatomy to be repaired. Finally, a replica of the template is produced by using Solid Freeform Fabrication manufacturing techniques.

Other features of embodiments of the present invention will be apparent from the accompanying drawings and from the detailed description that follows.

DETAILED DESCRIPTION

Systems and methods for designing and producing custom-made templates for implantation or pre-contouring metallic or polymer implantable plates prior to surgery are described. Broadly stated, embodiments of the present invention make use of sophisticated software packages and rapid prototyping processes to facilitate the design and production of custom-made templates for implantation or for pre-contouring metallic or polymer implantable plates prior to surgery. According to one embodiment, instead of forming the plate at the time of surgery, the surgeon would bend the plate before surgery with a custom-made template designed with the surgeon's interaction using medical image data and Solid Freeform Fabrication ("SFF") techniques (see e.g., Wohlers Report 2002, published by Wohlers Associates, Inc., April 2002, 250 pages, softbound).

According to one embodiment, results of an outsourced medical modeling service may be provided via an Extranet, a secure portal, a Virtual Private Network (VPN), or other communication infrastructure designed to carry data between or among computers.

In the following description, for the purposes of explanation, numerous specific details are set forth in order to provide a thorough understanding of embodiments of the present invention. It will be apparent, however, to one skilled in the art that embodiments of the present invention may be practiced without some of these specific details. In other instances, well-known structures and devices are shown in block diagram form.

Embodiments of the present invention include various steps, which will be described below. The steps may be performed by hardware components or may be embodied in machine-executable instructions, which may be used to cause a general-purpose or special-purpose processor programmed with the instructions to perform the steps. Alternatively, the steps may be performed by a combination of hardware and software.

Embodiments of the present invention may be provided in whole or in part as a computer program product which may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), and magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments of the present invention may also be downloaded as a computer program product, wherein the program may be transferred from a remote computer to a requesting computer by way of data signals embodied in a carrier wave or other propagation medium via a communication link (e.g., a modem or network connection).

While, for convenience, embodiments of the present invention are described with reference to design and manufacture of custom-made templates for pre-contouring implantable plates prior to surgery, embodiments of the present invention are equally applicable to directly implantable templates.

Terminology

Brief definitions of terms used throughout this application are given below.

The terms "connected" or "coupled" and related terms are used in an operational sense and are not necessarily limited to a direct connection or coupling.

The term "implant" generally refers to a surgically implanted structure or device, such as a dental implant a subcutaneous implant, or a prosthesis. Examples of implants include cranioplasty prostheses, facial implants for reconstruction of the oral and/or maxillofacial region, orthopedic implants and the like.

The phrases "in one embodiment," "according to one embodiment," and the like generally mean the particular feature, structure, or characteristic following the phrase is included in at least one embodiment of the present invention, and may be included in more than one embodiment of the present invention. Importantly, such phases do not necessarily refer to the same embodiment.

If the specification states a component or feature "may", "can", "could", or "might" be included or have a characteristic, that particular component or feature is not required to be included or have the characteristic.

The term "responsive" includes completely or partially responsive.

Overview

The method described herein, according to one embodiment of the present invention, allows the surgeon to go into surgery with a computer-designed, custom-made template for direct implantation or a pre-contoured metallic or polymer implantable plate formed with the aid of a computer-designed, custom-made template.

Further details regarding the steps in the described new method of design and production of these templates, according to one embodiment of the present invention, are provided in the above-referenced provisional patent application which has been incorporated by reference herein.

In the foregoing specification and in the provisional patent application incorporated herein, the invention is described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

What is claimed is:

1. A method of producing a template for use in pre-contouring bone reconstruction plates, the method comprising:
   receiving medical image data representing surrounding portions of a patient's anatomy to be repaired by surgical implantation of a bone reconstruction plate;
   performing three-dimensional surface reconstruction based on the medical image data;
   performing virtual removal of a bone or portion thereof to be reconstructed with reference to the medical image data by simulating the surgical implantation procedure;
   creating a representation of a template contoured to fit the patient's anatomy to be repaired; and
   outputting a replica of the template by using Solid Freeform Fabrication manufacturing techniques.

* * * * *